(12) United States Patent
Denham et al.

(10) Patent No.: US 10,130,355 B2
(45) Date of Patent: Nov. 20, 2018

(54) FLEXIBLE PLANAR MEMBER FOR TISSUE FIXATION

(71) Applicant: Biomet Sports Medicine, LLC, Warsaw, IN (US)

(72) Inventors: Gregory J. Denham, Warsaw, IN (US); Kevin T. Stone, Winona Lake, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 293 days.

(21) Appl. No.: 14/982,926

(22) Filed: Dec. 29, 2015

(65) Prior Publication Data

US 2016/0128683 A1 May 12, 2016

Related U.S. Application Data

(62) Division of application No. 13/610,196, filed on Sep. 11, 2012, now Pat. No. 9,232,939.

(51) Int. Cl.
*A61B 17/04* (2006.01)
*A61B 17/06* (2006.01)

(52) U.S. Cl.
CPC .... *A61B 17/0401* (2013.01); *A61B 2017/042* (2013.01); *A61B 2017/0404* (2013.01); *A61B 2017/0409* (2013.01); *A61B 2017/0414* (2013.01); *A61B 2017/0417* (2013.01); *A61B 2017/06185* (2013.01)

(58) Field of Classification Search
CPC ........ A61B 17/0401; A61B 2017/0409; A61B 2017/0417; A61B 2017/042; A61B 2017/0422; A61B 2017/0424; A61B 2017/0404; A61B 2017/0414; A61B 2017/06185

See application file for complete search history.

(56) References Cited

U.S. PATENT DOCUMENTS

| | | | |
|---|---|---|---|
| 3,409,014 A | 11/1968 | Grant | |
| 5,041,129 A | 8/1991 | Hayhurst et al. | |
| 5,171,274 A | 12/1992 | Fluckiger et al. | |
| 5,219,359 A | 6/1993 | McQuilkin et al. | |

(Continued)

FOREIGN PATENT DOCUMENTS

| | | |
|---|---|---|
| EP | 2895080 A1 | 7/2015 |
| WO | WO-2004037094 A2 | 5/2004 |
| WO | WO-2014043193 A1 | 3/2014 |

OTHER PUBLICATIONS

"U.S. Appl. No. 13/610,196, Examiner Interview Summary dated Jun. 9, 2015", 3 pgs.

(Continued)

*Primary Examiner* — Ryan J Severson
*Assistant Examiner* — Christian Knauss
(74) *Attorney, Agent, or Firm* — Schwegman Lundberg & Woessner, P.A.

(57) ABSTRACT

A flexible fixation assembly including a flexible main body and a suture engagement portion of the flexible main body. The suture engagement portion is configured to cooperate with a suture to mate the suture with the flexible main body. The flexible main body is configured to flex outward against walls of a bone hole when implanted therein to retain both the flexible main body and the suture mated therewith within the bone hole.

12 Claims, 15 Drawing Sheets

(56) References Cited

U.S. PATENT DOCUMENTS

| | | | |
|---|---|---|---|
| 5,403,348 A | 4/1995 | Bonutti | |
| 5,593,425 A * | 1/1997 | Bonutti | A61B 17/0401 606/220 |
| 5,662,681 A | 9/1997 | Nash et al. | |
| 5,716,408 A | 2/1998 | Eldridge et al. | |
| 5,984,926 A | 11/1999 | Jones | |
| 5,989,252 A | 11/1999 | Fumex | |
| 6,203,572 B1 | 3/2001 | Johnson et al. | |
| 6,280,477 B1 | 8/2001 | Mastrorio et al. | |
| 6,491,714 B1 | 12/2002 | Bennett | |
| 6,511,498 B1 | 1/2003 | Fumex | |
| 6,592,609 B1 | 7/2003 | Bonutti | |
| 6,602,290 B2 | 8/2003 | Esnouf et al. | |
| 6,656,182 B1 | 12/2003 | Hayhurst | |
| 6,746,483 B1 | 6/2004 | Bojarski et al. | |
| 7,001,390 B2 | 2/2006 | Gebhardt et al. | |
| 7,279,008 B2 | 10/2007 | Brown et al. | |
| 7,407,512 B2 | 8/2008 | Bojarski et al. | |
| 7,500,983 B1 | 3/2009 | Kaiser et al. | |
| 7,601,165 B2 | 10/2009 | Stone | |
| 7,658,751 B2 | 2/2010 | Stone et al. | |
| 7,731,750 B2 | 6/2010 | Bojarski et al. | |
| 7,740,657 B2 | 6/2010 | Brown, Jr. et al. | |
| 7,749,250 B2 | 7/2010 | Stone et al. | |
| 7,758,642 B2 | 7/2010 | Bojarski et al. | |
| 7,905,903 B2 | 3/2011 | Stone et al. | |
| 9,232,939 B2 | 1/2016 | Denham et al. | |
| 2001/0056287 A1 | 12/2001 | Bonutti | |
| 2003/0191498 A1 | 10/2003 | Foerster et al. | |
| 2004/0138707 A1 | 7/2004 | Greenhalgh | |
| 2005/0149115 A1 | 7/2005 | Roue et al. | |
| 2005/0267533 A1 | 12/2005 | Gertner | |
| 2005/0283246 A1 | 12/2005 | Cauthen, III et al. | |
| 2006/0030884 A1 * | 2/2006 | Yeung | A61B 17/0401 606/232 |
| 2007/0005068 A1 | 1/2007 | Sklar | |
| 2007/0067040 A1 | 3/2007 | Ferree | |
| 2007/0167982 A1 | 7/2007 | Gertner et al. | |
| 2007/0173888 A1 | 7/2007 | Gertner et al. | |
| 2008/0065114 A1 | 3/2008 | Stone et al. | |
| 2009/0306711 A1 * | 12/2009 | Stone | A61B 17/0401 606/232 |
| 2010/0222826 A1 | 9/2010 | Bojarski et al. | |
| 2010/0268275 A1 | 10/2010 | Stone et al. | |
| 2010/0324596 A1 | 12/2010 | Yeung et al. | |
| 2010/0324608 A1 | 12/2010 | Albertorio et al. | |
| 2011/0098727 A1 | 4/2011 | Kaiser et al. | |
| 2011/0106177 A1 | 5/2011 | Lewis | |
| 2011/0218625 A1 | 9/2011 | Berelsman et al. | |
| 2012/0290004 A1 * | 11/2012 | Lombardo | A61B 17/0401 606/232 |
| 2014/0074160 A1 | 3/2014 | Denham et al. | |

OTHER PUBLICATIONS

"U.S. Appl. No. 13/610,196, Examiner Interview Summary dated Oct. 28, 2014", 3 pgs.

"U.S. Appl. No. 13/610,196, Non Final Office Action dated Jan. 23, 2015", 17 pgs.

"U.S. Appl. No. 13/610,196, Non Final Office Action dated Jul. 22, 2014", 20 pgs.

"U.S. Appl. No. 13/610,196, Notice of Allowance dated Sep. 8, 2015", 11 pgs.

"U.S. Appl. No. 13/610,196, Response filed May 26, 2015 to Non Final Office Action dated Jan. 23, 2015", 14 pgs.

"U.S. Appl. No. 13/610,196, Response filed Jul. 7, 2014 to Restriction Requirement dated May 7, 2014", 10 pgs.

"U.S. Appl. No. 13/610,196, Response filed Oct. 22, 2014 to Non Final Office Action dated Jul. 22, 2014", 11 pgs.

"U.S. Appl. No. 13/610,196, Restriction Requirement dated May 7, 2014", 10 pgs.

"International Application Serial No. PCT/US2013/059200, International Preliminary Report on Patentability dated Mar. 17, 2015", 7 pgs.

"International Application Serial No. PCT/US2013/059200, International Search Report dated Jan. 18, 2014", 6 pgs.

"International Application Serial No. PCT/US2013/059200, Written Opinion dated Jan. 18, 2014", 6 pgs.

"European Application Serial No. 13773904.1, Communication Pursuant to Article 94(3) EPC dated Sep. 5, 2017", 5 pgs.

"European Application Serial No. 13773904.1, Communication Pursuant to Article 94(3) EPC dated Dec. 9, 2016", 4 pgs.

"European Application Serial No. 13773904.1, Communication pursuant to Rules 161(1) and 162 EPC dated May 29, 2015", 2 pgs.

"European Application Serial No. 13773904.1, Response filed Apr. 19, 2017 to Communication Pursuant to Article 94(3) EPC dated Dec. 9, 2016", 10 pgs.

"European Application Serial No. 13773904.1, Response filed Dec. 8, 2015 to Communication pursuant to Rules 161(1) and 162 EPC dated May 29, 2015", 11 pgs.

\* cited by examiner

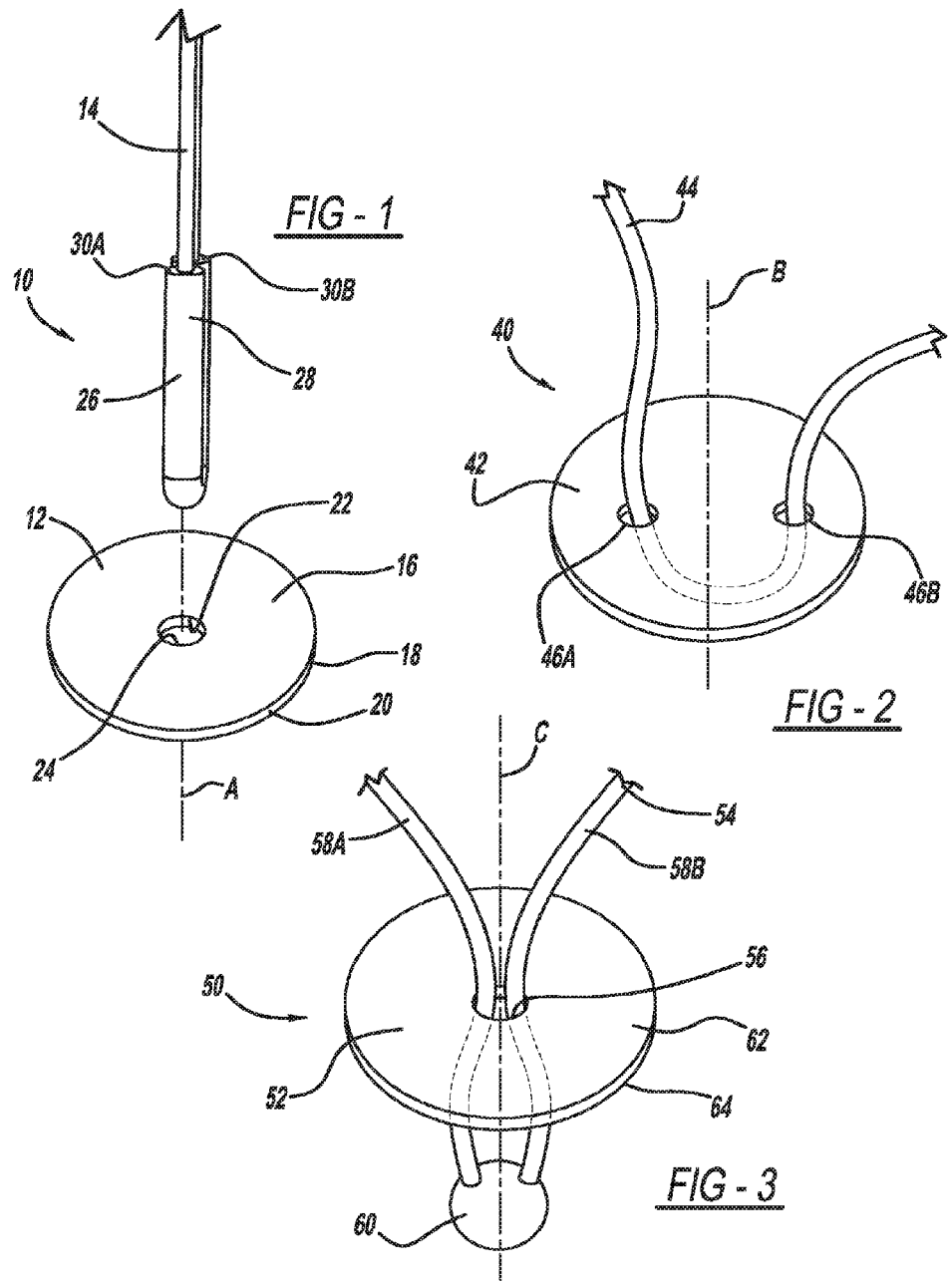

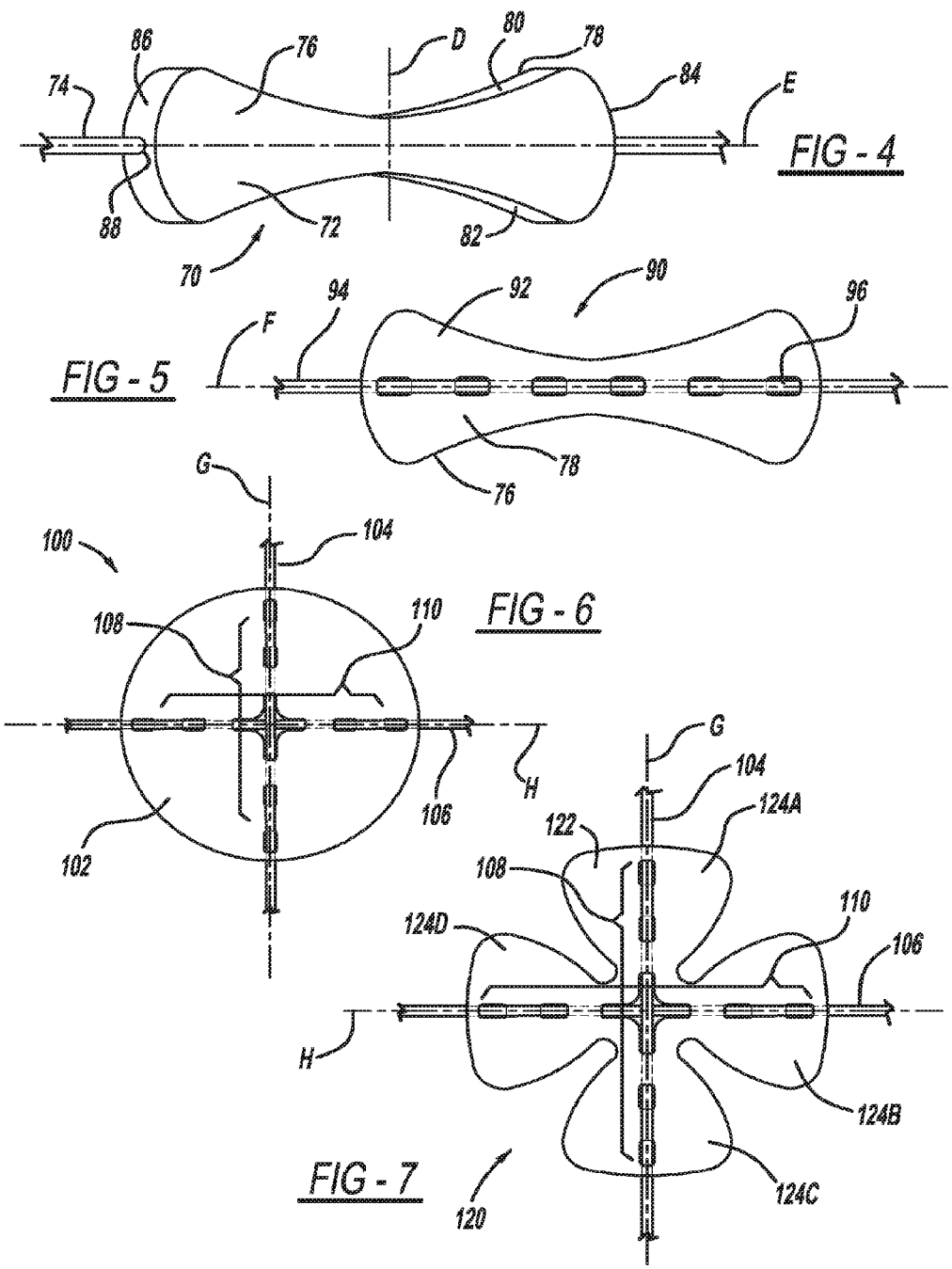

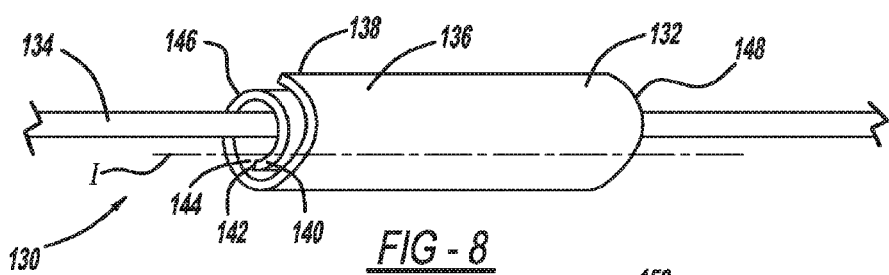
FIG-8
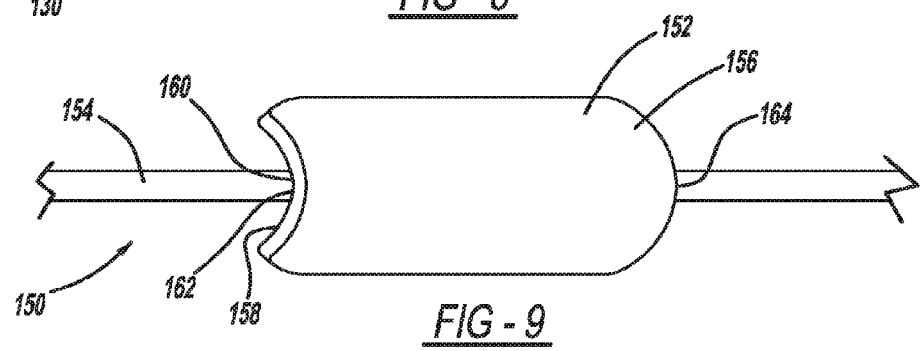
FIG-9
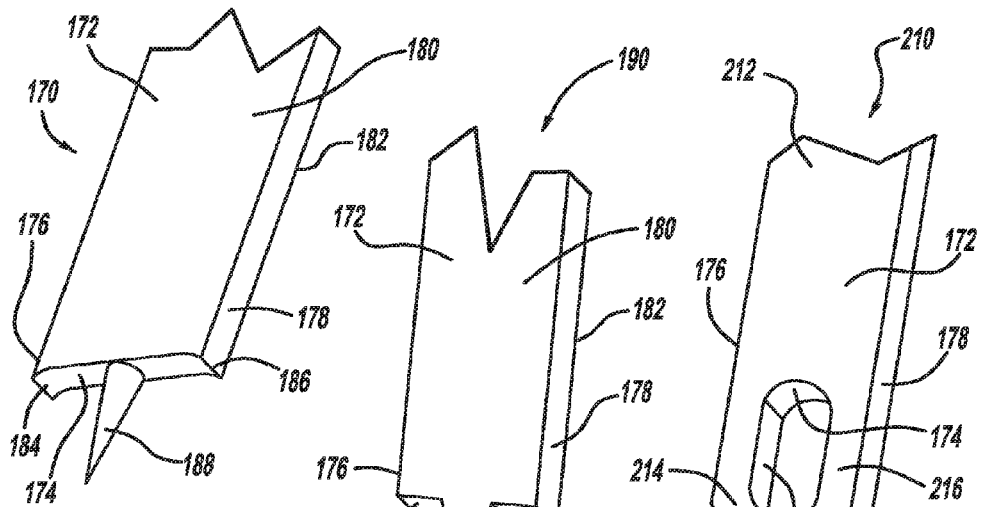
FIG-10
FIG-11
FIG-12

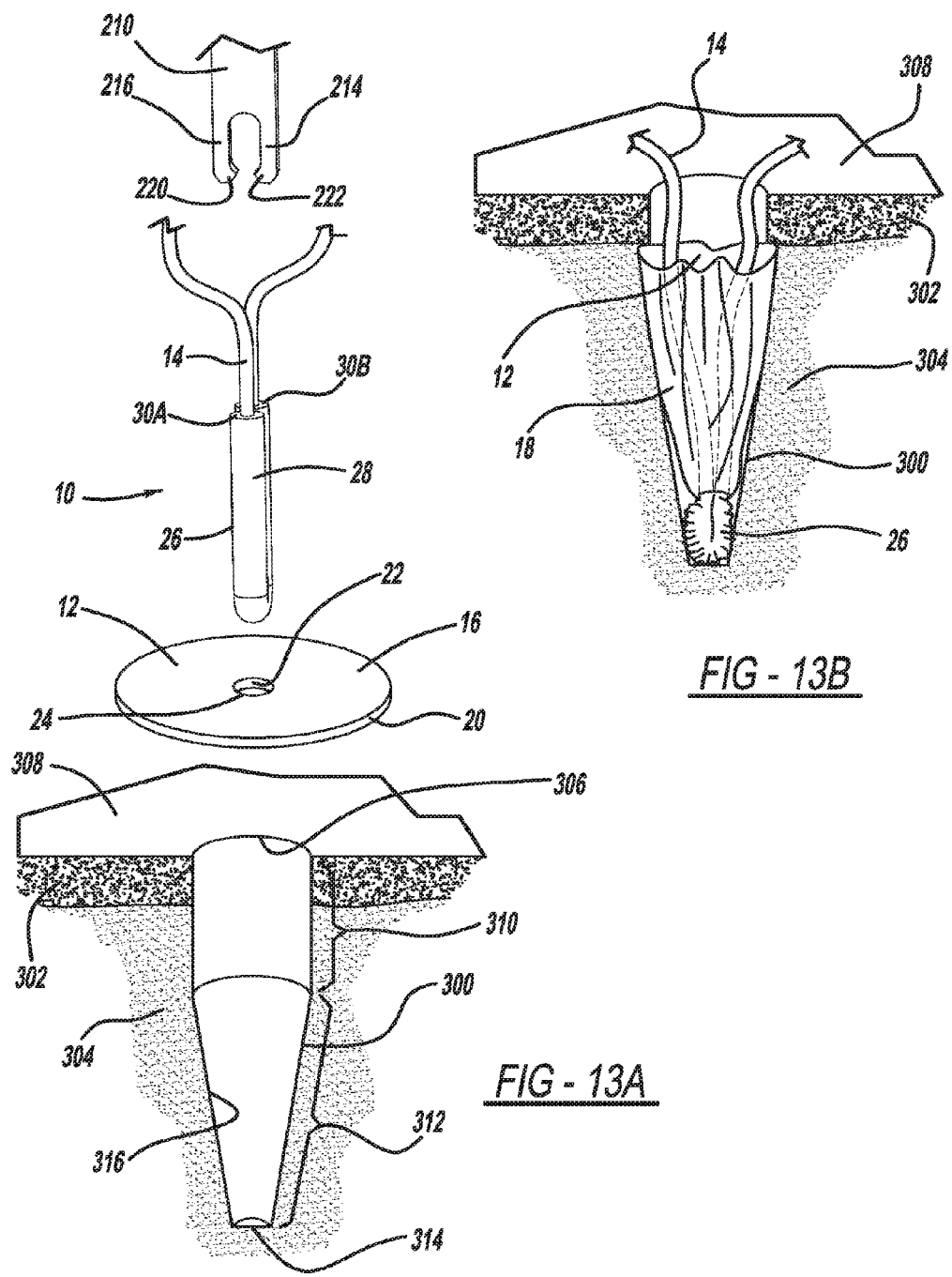

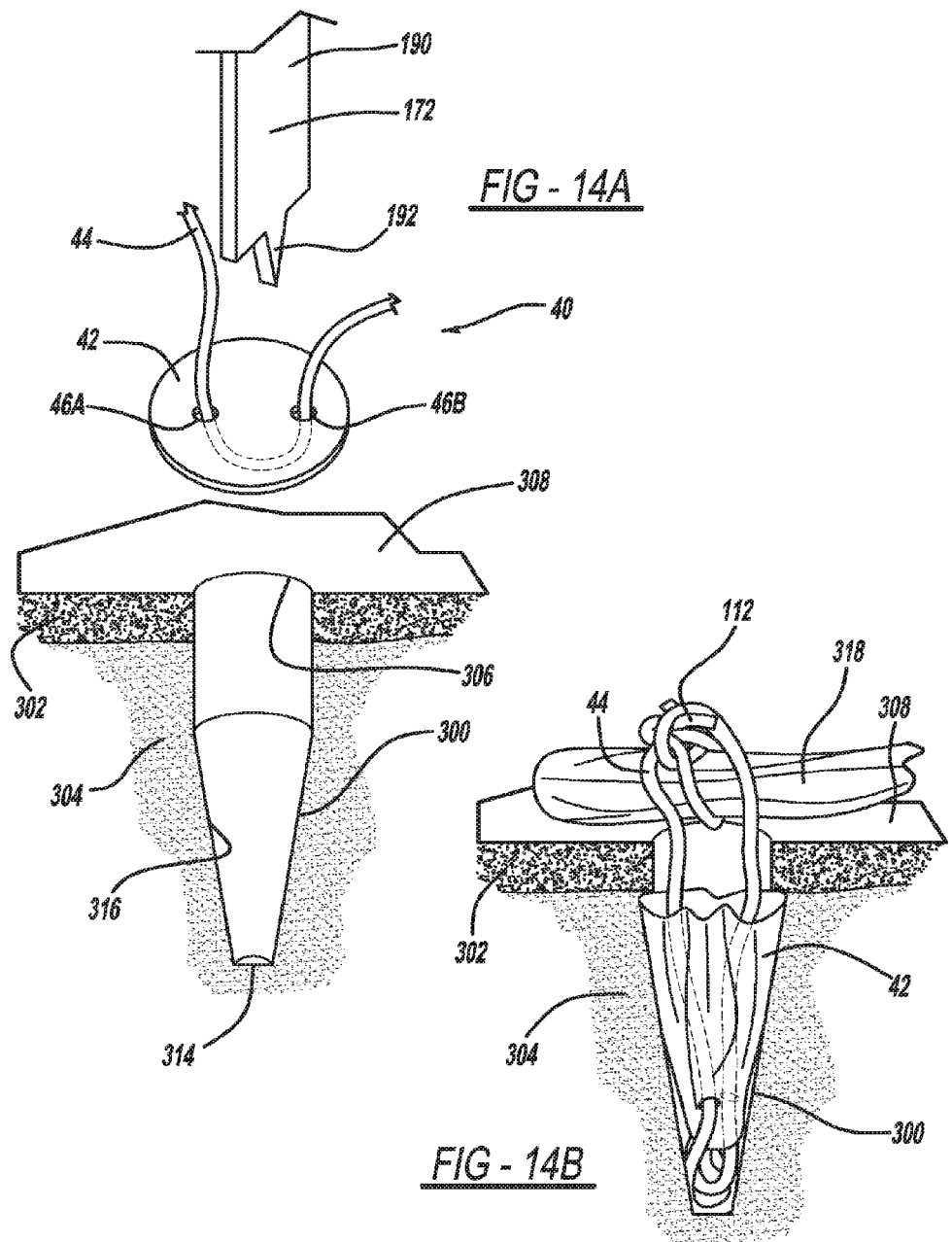

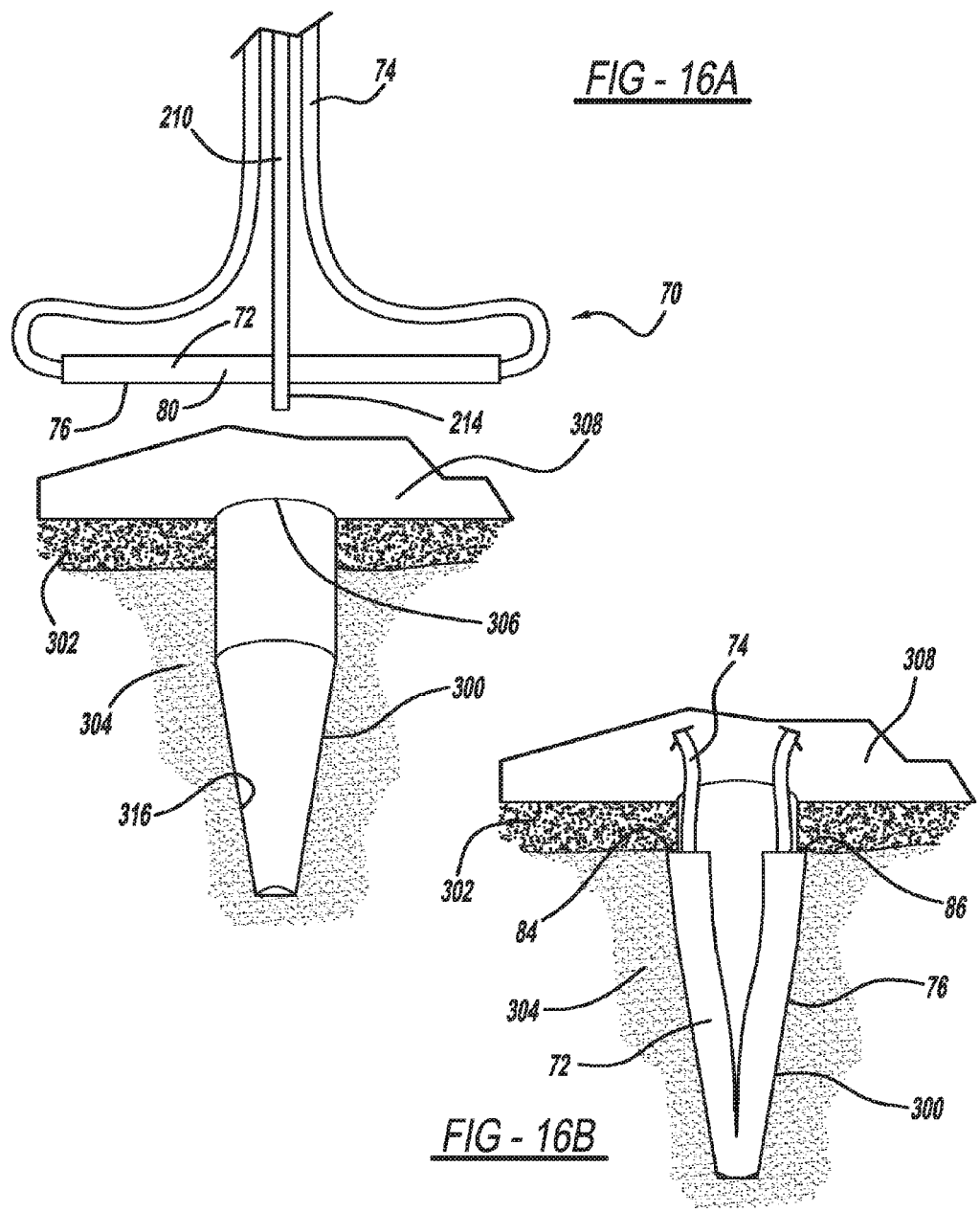

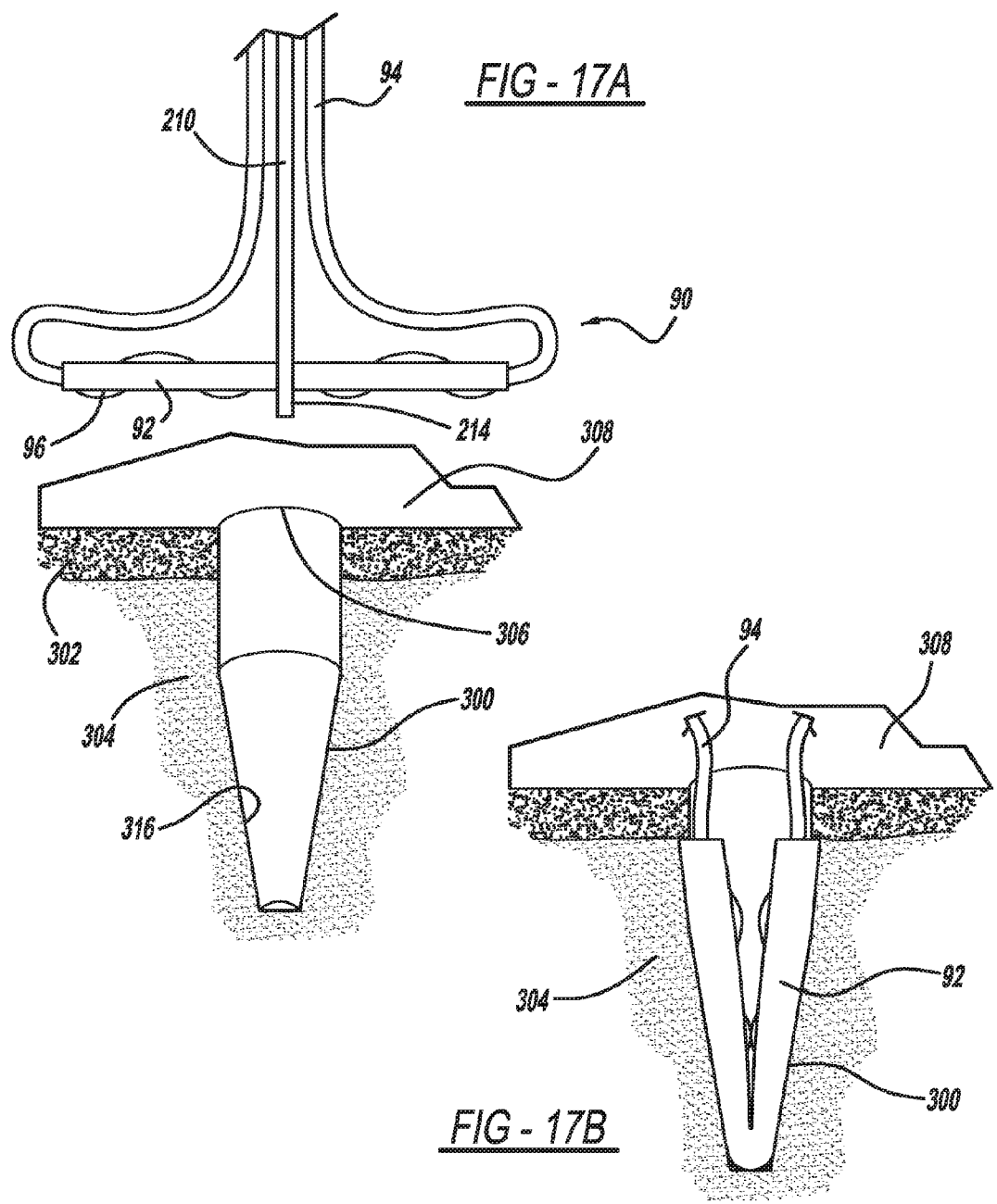

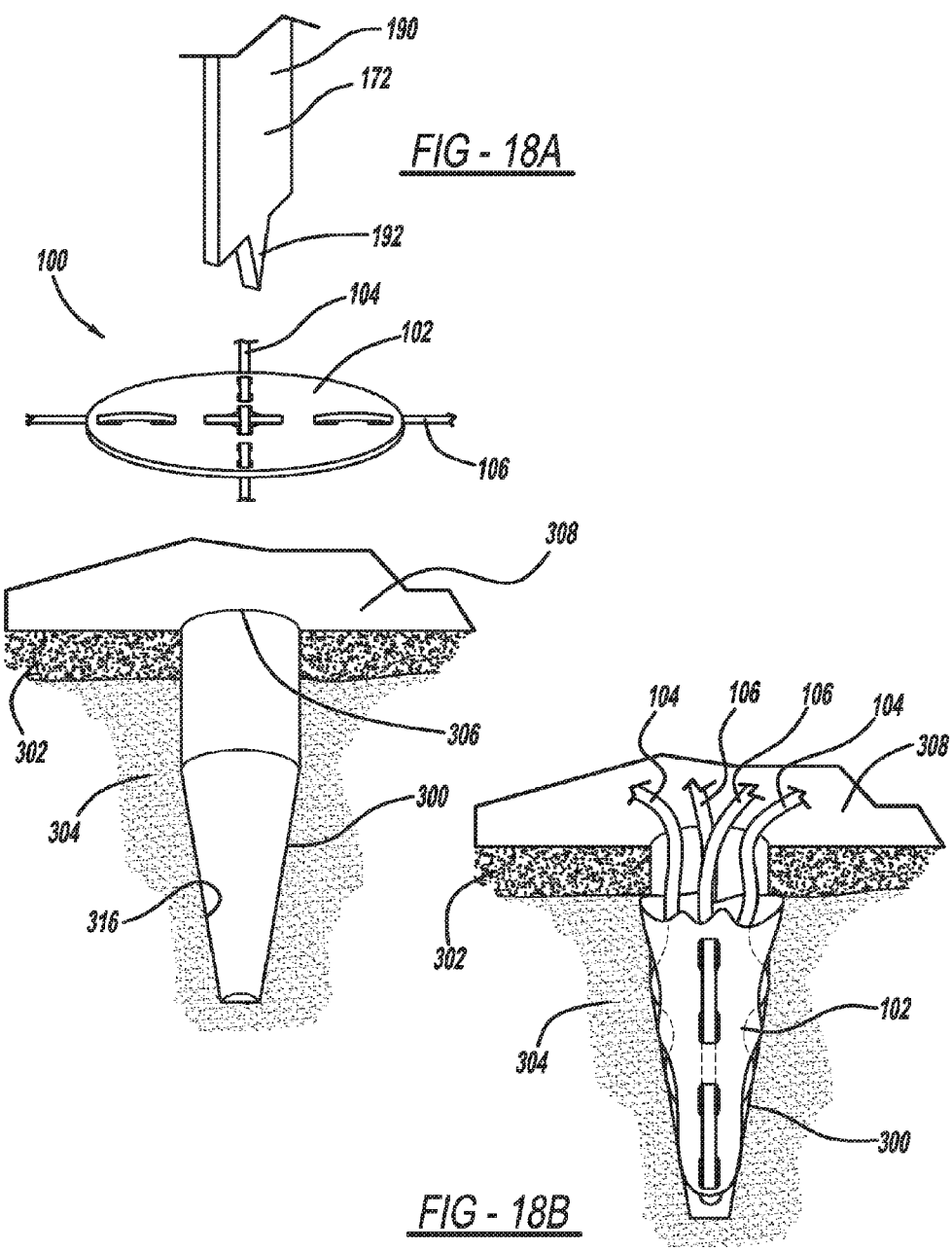

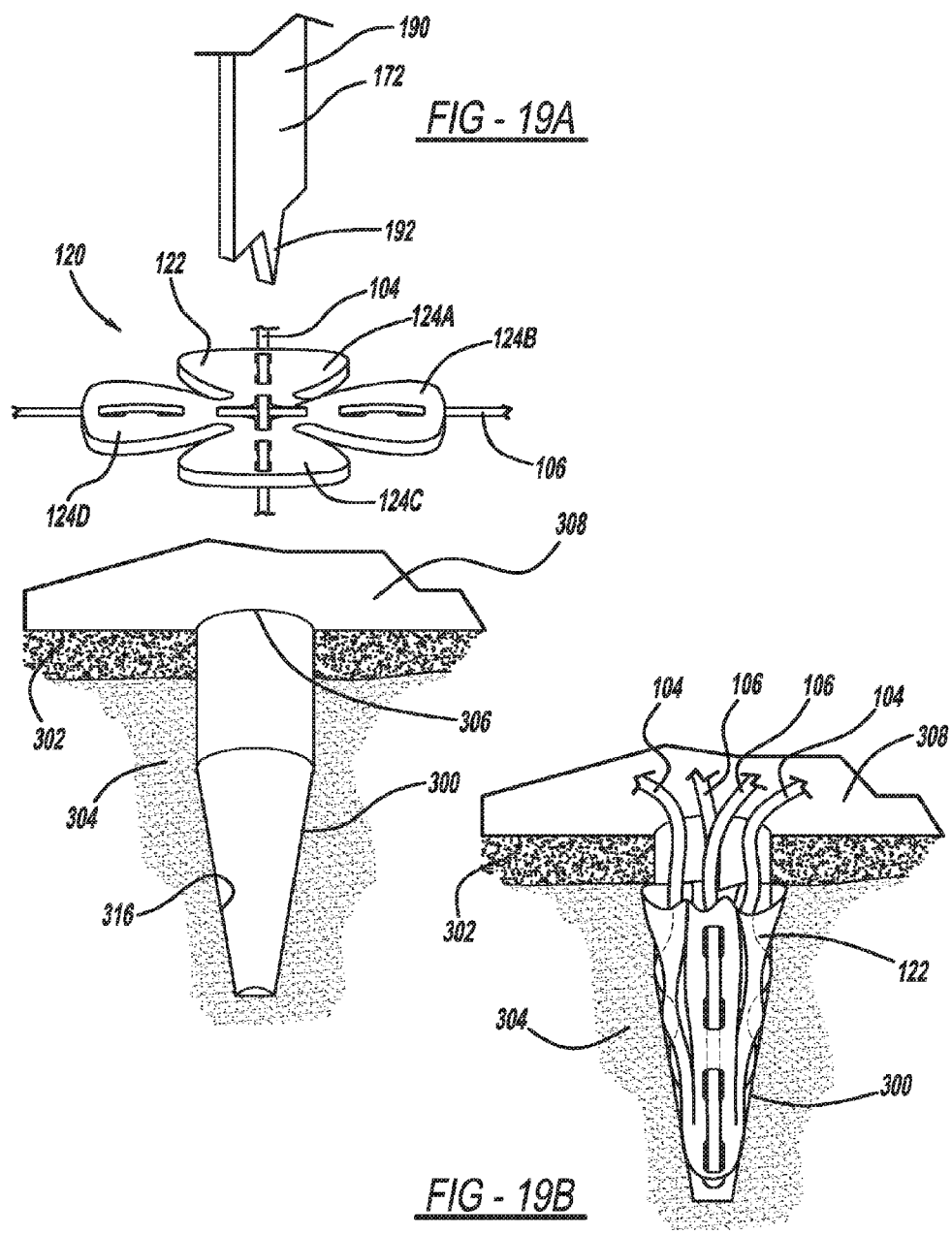

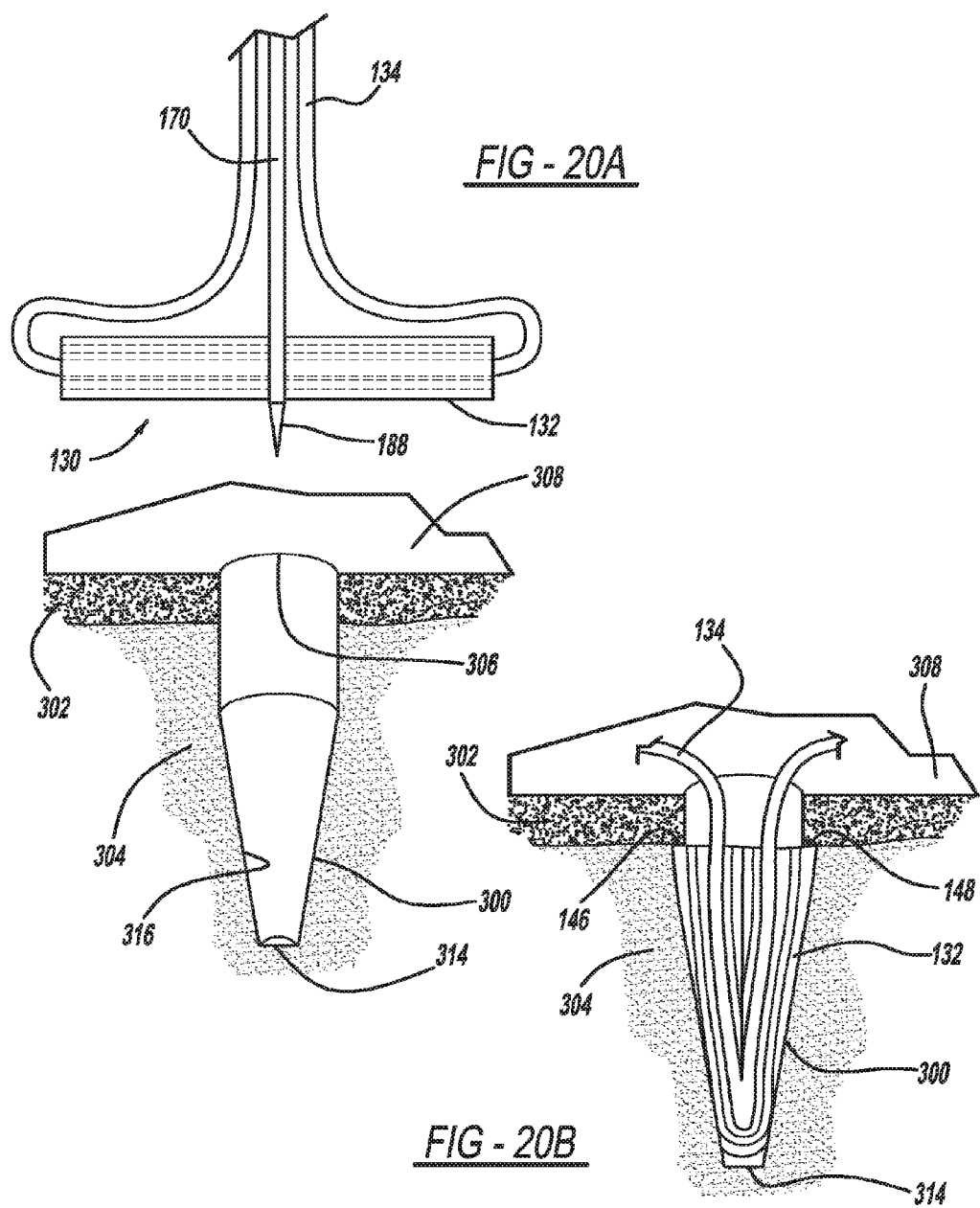

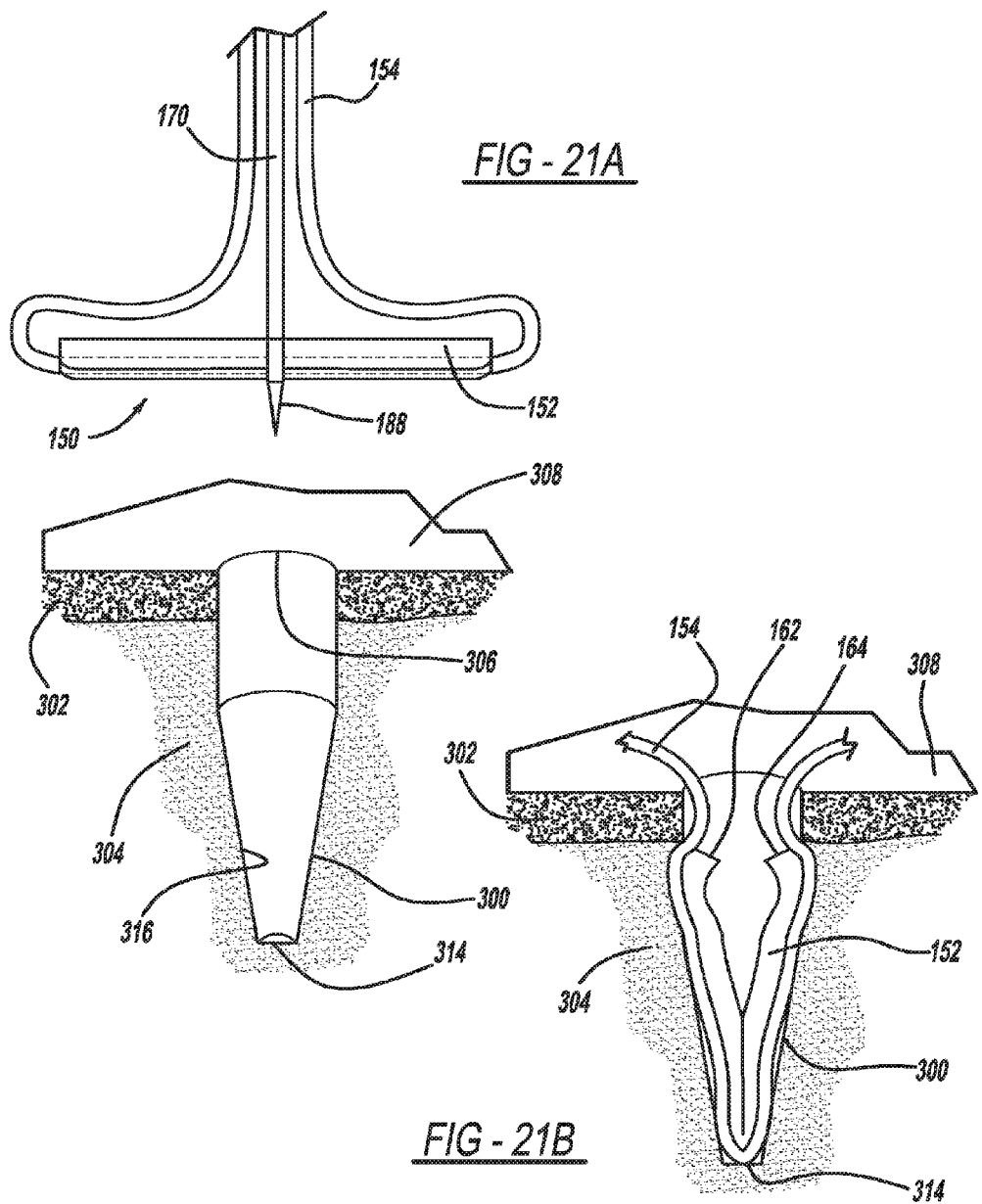

FLEXIBLE PLANAR MEMBER FOR TISSUE FIXATION

CLAIM OF PRIORITY

This application is a divisional of U.S. patent application Ser. No. 13/610,196, filed on Sep. 11, 2012, now issued as U.S. Pat. No. 9,232,939, the benefit of priority of which is claimed hereby, and which is incorporated by reference herein in its entirety.

FIELD

The present disclosure relates to a flexible planar member for tissue fixation.

BACKGROUND

This section provides background information related to the present disclosure which is not necessarily prior art.

Various devices exist to attach tissue to bone. Most devices include a molded or machined component that is rigid. For example, to attach soft tissue to bone a rigid anchor is often used. Such rigid members can be difficult to implant and often provide inconsistent fixation. Applicant's invention includes a flexible fixation member, which can be easily implanted in a bone hole as an anchor for a suture, for example. The suture can be used to affix a variety of tissues and implants.

SUMMARY

This section provides a general summary of the disclosure, and is not a comprehensive disclosure of its full scope or all of its features.

The present teachings provide for a flexible fixation assembly including a flexible main body and a suture engagement portion. The flexible main body includes a first generally planar surface, a second generally planar surface, and a side surface. The second generally planar surface is opposite to, and spaced apart from, the first generally planar surface. The side surface extends between the first generally planar surface and the second generally planar surface. The suture engagement portion of the flexible main body is configured to cooperate with a suture to mate the suture with the flexible main body. The flexible main body is configured to flex outward against walls of a bone hole when implanted therein to retain both the flexible main body and the suture mated therewith within the bone hole.

The present teachings also provide for a method for affixing a suture in a bone hole. The method includes forming a bone hole in bone; positioning at the bone hole a flexible main body having a suture attached to a suture engagement portion of the flexible main body, the flexible main body including a first generally planar surface, a second generally planar surface opposite to and spaced apart from the first generally planar surface, and a side surface extending between the first generally planar surface and the second generally planar surface; and implanting within the bone hole the flexible main body with the suture coupled thereto using an insertion tool such that the first generally planar surface and the second generally planar surface each move to a collapsed non-planar position as implanted, the flexible main body configured to flex outward against walls of the bone hole to retain the flexible main body and the suture coupled thereto within the bone hole.

The present teachings also provide for a method for affixing a suture in a bone hole. The method includes forming a bone hole in bone; positioning at the bone hole a flexible main body having a suture coupled thereto, the flexible main body in a first configuration in which a first surface and a second surface opposite to the first surface are each generally planar; inserting the flexible main body with the suture coupled thereto in the bone hole with the insertion tool such that as the flexible main body is inserted the flexible main body folds at a point where the insertion tool is connected to the flexible main body to provide the flexible main body with a second configuration in which the first surface and the second surface are not planar; and coupling soft tissue to the suture to secure the soft tissue within or proximate to the bone hole.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a flexible fixation assembly according to the present teachings;

FIG. 2 is a perspective view of another flexible fixation assembly according to the present teachings;

FIG. 3 is a perspective view of an additional flexible fixation assembly according to the present teachings;

FIG. 4 is a perspective view of yet another flexible fixation assembly according to the present teachings;

FIG. 5 is a planar view of a further flexible fixation assembly according to the present teachings;

FIG. 6 is a planar view of another flexible fixation assembly according to the present teachings;

FIG. 7 is a planar view of an additional flexible fixation assembly according to the present teachings;

FIG. 8 is a perspective view of a further flexible fixation assembly according to the present teachings;

FIG. 9 is a perspective view of another flexible fixation assembly according to the present teachings;

FIG. 10 is a perspective view of a distal portion of an insertion tool according to the present teachings;

FIG. 11 is a perspective view of a distal portion of another insertion tool according to the present teachings;

FIG. 12 is a perspective view of a distal portion of yet another insertion tool according to the present teachings;

FIGS. 13A and 13B illustrate insertion of the flexible fixation assembly of FIG. 1 within a bone hole with the insertion tool of FIG. 12;

FIGS. 14A and 14B illustrate insertion of the flexible fixation assembly of FIG. 2 within a bone hole with the insertion tool of FIG. 11;

FIGS. 16A and 16B illustrate insertion of the flexible fixation assembly of FIG. 4 within a bone hole with the insertion tool of FIG. 11;

FIGS. 17A and 17B illustrate insertion of the flexible fixation assembly of FIG. 5 within a bone hole with the insertion tool of FIG. 12;

FIGS. 18A and 18B illustrate insertion of the flexible fixation assembly of FIG. 6 within a bone hole with the insertion tool of FIG. 11;

FIGS. 19A and 19B illustrate insertion of the flexible fixation assembly of FIG. 7 within a bone hole with the insertion tool of FIG. 11;

FIGS. 20A and 20B illustrate insertion of the flexible fixation assembly of FIG. 8 within a bone hole with the insertion tool of FIG. 11, FIG. 20B is a cross-sectional view of the flexible fixation assembly implanted in the bone hole;

FIGS. 21A and 21B illustrate insertion of the flexible fixation assembly of FIG. 9 within a bone hole with the insertion tool of FIG. 11;

Corresponding reference numerals indicate corresponding parts throughout the several views of the drawings.

DETAILED DESCRIPTION

Figures 15A, 15B:
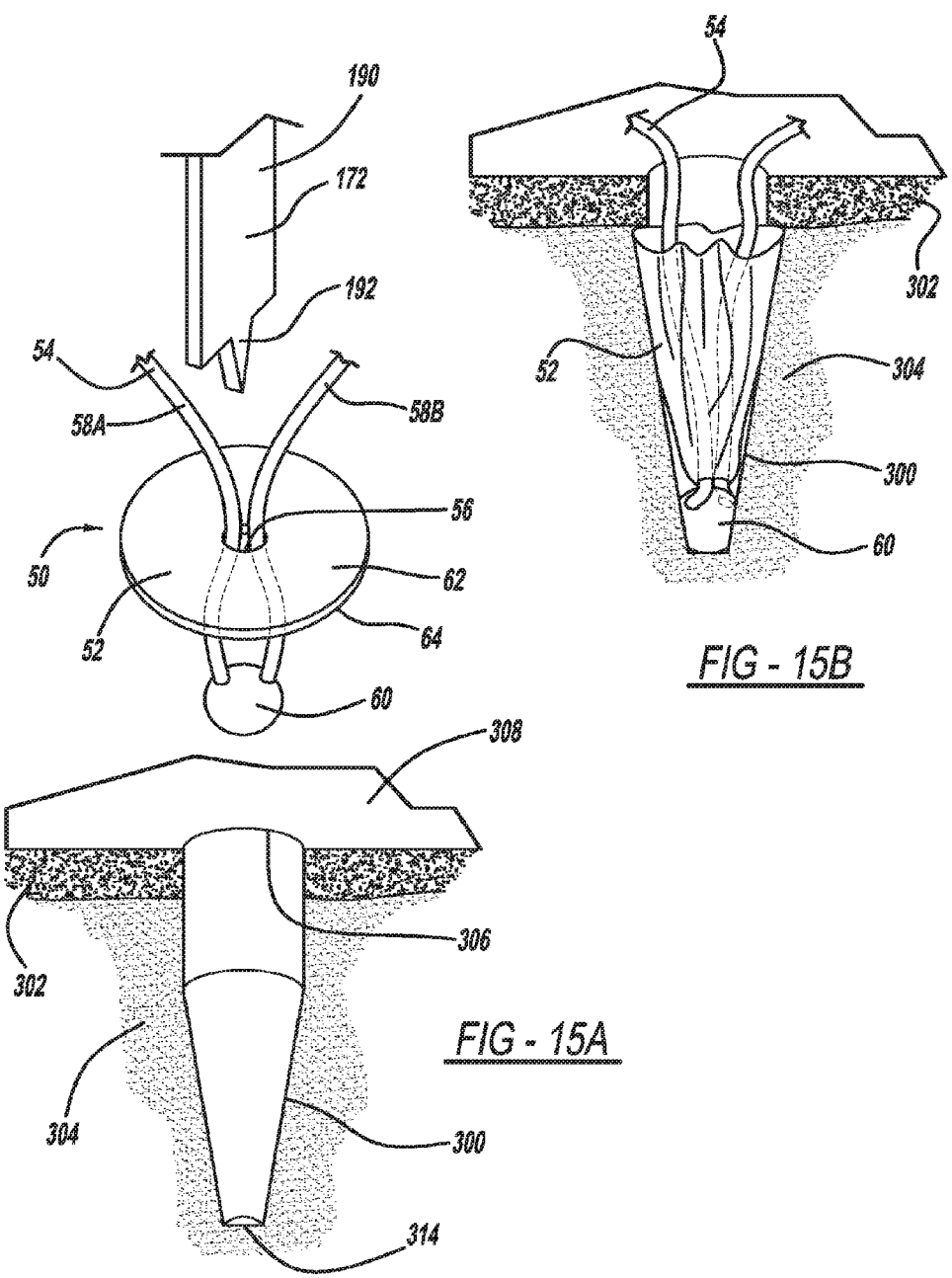
FIGS. 15A and 15B illustrate insertion of the flexible fixation assembly of FIG. 3 within a bone hole with the insertion tool of FIG. 11.

Example embodiments will now be described more fully with reference to the accompanying drawings.

With initial reference to FIG. 1 a flexible fixation assembly according to the present teachings is generally illustrated at reference numeral 10. The flexible fixation assembly 10 generally includes a flexible main body 12 and a suture or suitable flexible strand 14.

The flexible main body 12 is generally annular and includes a first surface 16 and a second surface 18 that is opposite to the first surface 16. The first surface 16 and the second surface 18 are both generally planar in an unflexed condition (first configuration). The first surface 16 and the second surface 18 extend in spaced apart planes that extend generally parallel to each other. At an outer circumference of the flexible main body 12 is an outer peripheral edge 20. At an inner circumference of the flexible main body 12 is an inner edge 22. The inner edge 22 defines an aperture 24 at an axial center of the flexible main body 12. Axis A extends through the axial center perpendicular to the generally planar first surface 16 and the generally planar second surface 18. The aperture 24 forms a suture engagement or connection portion for connecting the suture 14 to the flexible main body 12, as further described herein. Therefore, reference number 24 also designates the suture engagement or connection portion of the flexible main body 12. The distance between the first surface 16 and the second surface 18, which defines a thickness of the flexible main body 12, can be any suitable distance, and the first and the second surfaces 16 and 18 can have any suitable surface area. The thickness and the surface area can be dependent on one another or proportional. The thickness can be from about 0.1 mm to about 2.4 mm thick, for example. The diameter of each of the first and the second surfaces 16 and 18 can be from about 2 mm to about 48 mm, for example.

The flexible main body 12 can be made of any suitable shape, size, and material such that when the flexible main body 12 is inserted in a cavity having a diameter smaller than a diameter of the flexible main body 12, such as a bone hole for example, the first surface 16 will be forced inward upon the axis A to provide the flexible main body 12 in a flexed position (second configuration) and the outer peripheral edge 20 will be biased to expand outward against interior walls of the bone hole to retain the flexible main body 12 within the bone hole, as further described herein. The flexible main body 12 can also be configured to be implanted within material other than bone, such as soft tissue, including the meniscus for example. The flexible main body 12 can include, for example, a material that is woven, knit, braided, or solid. Further, the flexible main body 12 can include, for example, felt, polyester, polypropylene, polyethylene, PEEK, nylon, xenograft mesh, allograft mesh, or SportMesh™ by Biomet, Inc. of Warsaw, Indiana. The flexible main body 12 may be porous, perforated, textured, barbed, expandable, bonding, contain Biologic elements, include zones having a greater propensity to flex, include planar surfaces formed to flex into the same end shape, e.g. a dome, and include a pre-flexing body to facilitate implantation.

The suture 14 generally includes a suture anchor 26 mounted thereto. Any suitable suture 14 can be used, such as the MaxBraid™ Suture from Biomet, Inc. of Warsaw, Ind., as disclosed in, for example, U.S. patent application Ser. No. 12/915,962 filed on Oct. 29, 2010, which is incorporated by reference herein. The suture anchor 26 generally includes a collapsible sleeve 28 through which the suture 14 is threaded. The collapsible sleeve 28 includes a first end 30A and a second end 30B. The suture anchor 26 can be any suitable anchor sufficient to anchor the suture 14 to the flexible main body 12 at the suture engagement portion 24. For example, the suture anchor 26 can be a soft anchor, such as the JuggerKnot™ soft anchor from Biomet, Inc. of Warsaw, Ind. To anchor the suture 14 to the flexible main body 12, the suture anchor 26 is inserted through the suture engagement portion 24 from the first surface 16 to the second surface 18. At the second surface 18 the collapsible sleeve 28 expands. The first end 30A and the second end 30B contact the second surface 18 proximate to the suture engagement portion 24 to prevent the suture anchor 26 from being pulled back out through the suture engagement portion 24.

With additional reference to FIG. 2, another flexible fixation assembly according to the present teachings is generally illustrated at reference numeral 40. The flexible fixation assembly 40 generally includes a flexible main body 42 and a suture 44. The flexible main body 42 is substantially similar to the flexible main body 12, and thus the description of the flexible main body 12 also describes the flexible main body 42. The flexible main body 42 differs from the flexible main body 12 in that the flexible main body 42 defines multiple apertures, a first aperture 46A and a second aperture 46B. Together, the first aperture 46A and the second aperture 46B provide a suture engagement or connection portion for connecting the suture 44 to the flexible main body 42. Therefore, reference numbers 46A and 46B together designate the suture engagement or connection portion of the flexible main body 42. To connect the suture 44 to the suture engagement portion 46A and 46B, the suture 44 is first partially threaded through the first aperture 46A and then back through the second aperture 46B, as illustrated in FIG. 2 for example.

With additional reference to FIG. 3, another flexible fixation assembly according to the present teachings is generally illustrated at reference numeral 50. The flexible fixation assembly 50 generally includes a flexible main body 52 and a suture 54. The flexible main body 52 is substantially similar to the flexible main body 12, and thus the description of the flexible main body 12 also applies to the flexible main body 52. The flexible main body 52 defines a single aperture 56 at an axial center of the flexible main body 52, through which axis C extends. The aperture 56 is a suture engagement portion for connecting the suture 54 to the flexible main body 52. The suture 54 includes a first strand 58A and a second strand 58B, each of which extend from a coupling or interference member 60. The coupling member 60 is generally spherical and has a diameter greater than a diameter of the aperture 56, which prevents the coupling member 60 from passing through the aperture 56. The suture 54 is arranged such that the first strand 58A and the second strand 58B extend through the aperture 56 beyond a first surface 62 of the flexible main body 52. The coupling member 60 is arranged opposite to a second surface 64 of the flexible main body 52. As a result, if the first and the second strands 58A and 58B are pulled, the coupling member 60 prevents the suture 54 from becoming detached from the flexible main body 52.

With additional reference to FIG. 4, another flexible fixation assembly according to the present teachings is generally illustrated at reference numeral 70. The flexible fixation assembly 70 generally defines an "hourglass" shape and generally includes a flexible main body 72 and a suture 74. The flexible main body 72 includes a first generally planar surface 76, a second generally planar surface 78 opposite to the first generally planar surface 76, a first tapered side surface 80, and a second tapered side surface 82 opposite to the first tapered side surface 80. The first tapered side surface 80 and the second tapered side surface 82 each extend between the first generally planar surface 76 and the second generally planar surface 78. The first tapered side surface 80 and the second tapered side surface 82 are tapered such that they are generally closest together along a line D located equidistant between a first end 84 of the flexible main body 72 and a second end 86 of the flexible main body 72. The flexible main body 72 can generally be made of the same materials as described above with respect to the flexible main body 12. To accommodate the suture 74, the flexible main body 72 is generally thicker at the first and the second ends 84 and 86 than the flexible main body 12 is at the outer peripheral edge 20.

The flexible main body 72 defines an aperture 88 extending between the first end 84 and the second end 86 of the flexible main body 72 along a longitudinal axis E of the flexible main body 72. The longitudinal axis E is generally perpendicular to the line D. The suture 74 is arranged such that it extends through the aperture 88 and the flexible main body 72 is slidably seated thereon. The aperture 88 is thus a suture engagement or connection portion for connecting the suture 74 to the flexible main body 72.

With additional reference to FIG. 5, another flexible fixation assembly according to the present teachings is generally illustrated at reference numeral 90. The flexible fixation assembly 90 generally includes a flexible main body 92 and a suture 94. The flexible main body 92 is substantially similar to the flexible main body 72, and thus the description of the flexible main body 72 also applies to the flexible main body 92 and like reference numbers are used to refer to similar features of the flexible main body 92. Unlike the flexible main body 72, however, the flexible main body 92 does not include the single aperture 88 extending along its longitudinal axis F. Instead, the flexible main body 92 defines a plurality of slits 96 extending along its longitudinal axis F. The suture 94 is threaded through the slits 96 to thereby connect the suture 94 to the flexible main body 92. For example, the suture 94 is threaded through the slits 96 in a weave-like manner such that the suture 94 protrudes in an alternating manner from the first and the second generally planar surfaces 76 and 78. The slits 96 are thus a suture engagement portion for connecting the suture 94 to the flexible main body 92. Therefore, the flexible fixation assembly 90 can be substantially thinner than the flexible fixation assembly 70.

With additional reference to FIG. 6, an additional flexible fixation assembly according to the present teachings is generally illustrated at reference numeral 100. The flexible fixation assembly 100 generally includes a flexible main body 102, a first suture 104, and a second suture 106. Thus the flexible main body 102 allows two sutures 104 and 106 to be anchored in a bone hole, as further described herein. The flexible main body 102 is generally similar to the flexible main body 12 of FIG. 1, and thus the description of the flexible main body 12 generally applies to the flexible main body 102. Unlike the flexible main body 12, however, the flexible main body 102 does not include the single aperture 24. Instead, the flexible main body 102 includes a first array of spaced apart slits 108 defined by the flexible main body 102 extending along a first line G, and a second array of spaced apart slits 110 defined by the flexible main body 102 extending along a second line H that is perpendicular to the first line G. The first suture 104 is threaded through the first array of spaced apart slits 108 to connect the first suture 104 to the flexible main body 102. The second suture 106 is threaded through the second array of spaced apart slits 110 to connect the second suture 106 to the flexible main body 102. The first and the second sutures 104 and 106 are threaded into the flexible main body 102 in generally the same manner that the suture 94 is threaded into the flexible main body 92, as described above. Thus, the first array of spaced apart slits 108 and the second array of spaced apart slits 110 are suture engagement portions for connecting the sutures 104 and 106 to the flexible main body 102.

With additional reference to FIG. 7, yet another flexible fixation assembly according to the present teachings is generally illustrated at reference numeral 120. The flexible fixation assembly 120 generally includes a flexible main body 122 that is substantially similar to the main body 102 of the flexible fixation assembly 100. Thus, the flexible main body 122 includes the first array of spaced apart slits 108 and the second array of spaced apart slits 110 orientated perpendicular to one another. The first suture 104 is threaded through the first array of spaced apart slits 108 and the second suture 106 is threaded through the second array of spaced apart slits 110, which allows two sutures to be secured to bone. Unlike the flexible main body 102, the flexible main body 122 is configured to define four radially extending wings 124A-124D that extend from a center of the flexible main body 122 where the first line G intersects the second line H.

With additional reference to FIG. 8, an additional flexible fixation assembly according to the present teachings is generally illustrated at reference numeral 130. The flexible fixation assembly 130 generally includes a flexible main body 132 and a suture 134. The flexible main body 132 is provided as a generally rectangular sheet including a first portion 136 proximate to a first end 138 and a second portion 140 proximate to a second end 142. The flexible main body is rolled or folded such that the first portion 136 overlaps the second portion 140 to define an aperture 144 extending through the flexible main body 132. The first portion 136 and the second portion 140 can be secured together with any suitable adhesive or mechanical fastening device. A longitudinal axis I extends along an axial center of the aperture 144. The suture 134 is arranged such that it extends through the aperture 144 along the longitudinal axis I to extend from a first side 146 to a second side 148 of the flexible main body 132. The suture 134 can either be attached to the flexible main body 132, such as with a suitable adhesive, or slidably seated within the aperture 144. The aperture 144 is a suture engagement portion for coupling the suture 134 to the flexible main body 132. The flexible main body 132 can be made of any suitable material, such as the same material that the flexible main body 12 can be made of, as described above in conjunction with the description of the flexible main body 12.

With additional reference to FIG. 9, still another flexible fixation assembly according to the present teachings is illustrated at reference numeral 150. The flexible fixation assembly 150 generally includes a flexible main body 152 and a suture 154. The flexible main body 152 generally includes a preformed convex outer surface 156 and a preformed concave inner surface 158 that is opposite to the convex outer surface 156. The flexible main body 152 can be made of any suitable material, such as the same material that the flexible main body 12 can be made of, as described above in conjunction with the description of the flexible main body 12. The suture 154 is arranged opposite to the concave inner surface 158 at a center or general trough 160 of the concave inner surface 158 such that the suture 154 extends between a first end 162 and a second end 164 of the flexible main body 152. The suture 154 can be fastened to the concave inner surface 158 with a suitable adhesive or mechanical fastening device, or oriented such that the suture 154 abuts the concave inner surface 158 or is in close proximity thereto. The concave inner surface 158 is thus a suture engagement portion of the flexible main body 152. As further described herein, the flexible fixation assembly 150 can be implanted in a bone hole by orientating the suture 154 across the bone hole, orienting the flexible main body 152 over the suture 154 such that the concave inner surface 158 faces the bone hole, and pushing the flexible main body 152 into the bone hole using a suitable insertion tool, such as one of the insertion tools 170. 190, 210 described herein. The flexible main body 152 is implanted such that the concave inner surface 158 enters the bone hole first. The insertion tool is thus orientated such that it pushes against the convex outer surface 156.

Features of the various flexible fixation assemblies 10, 40, 50, 70, 90, 100, 120, 130, and 150 can be interchanged to provide numerous configurations in addition to those illustrated. Thus, the suture engagement or connection portions 24, 46, 56, 88, 96, 108, 110, 144, 158 can be included with any one of the flexible fixation assemblies 10, 40, 50, 70, 90, 100, 120, 130, and 150. For example, the suture 44 of the flexible fixation assembly 40 can include the coupling member 60 of the assembly 50 to maintain cooperation between the suture 44 and the flexible main body 42. Also, while the flexible main body 72 of FIG. 4 is illustrated as including a single suture 74 extending through the aperture 88, the flexible main body 72 can define another aperture perpendicular to the aperture 88 along line D to accommodate another suture. The flexible main body 92 can also include an additional suture perpendicular to the suture 94, such as by threading the additional suture through one of the slits 96 in a direction perpendicular to the suture 94.

With additional reference to FIG. 10, an insertion tool is generally illustrated at reference numeral 170. The insertion tool 170 includes a handle 172 with a distal end 174 and a proximal end (not shown) opposite to the distal end 174. The handle 172 further includes a first side 176 opposite to a second side 178. Extending between the first side 176 and the second side 178 is a first planar surface 180 and a second planar surface 182 that is opposite to the first planar surface 180. Extending from the first side 176 at the distal end 174 is a first retention surface 184 in the form of a ridge that protrudes from the distal end 174. Extending from the second side 178 at the distal end 174 is a second retention surface 186 in the form of a ridge that protrudes from the distal end 174. Also extending from the distal end 174 approximately equidistant between the first and the second retention surfaces 184 and 186 is a pointed conical tip 188. The pointed conical tip 188 and the first and second retention surfaces 184 and 186 are configured to facilitate engagement with any of the flexible main body members 12, 42, 52, 72, 92, 102, 122, 132, 152 described herein to retain the flexible main body members at the distal end 174 during implantation in a bone hole, for example.

With additional reference to FIG. 11, another insertion tool according to the present teachings is generally illustrated at reference numeral 190. The insertion tool 190 is similar to the insertion tool 170, and thus like reference numbers are used to designate the similar features. Unlike the insertion tool 170, the insertion tool 190 includes a pointed tip 192 that is not conical, but rather includes a first planar tip surface 194 that is coplanar with the first planar surface 180 of the handle 172 and a second planar tip surface 196 that is coplanar with the second planar surface 182. Extending between the first and the second planar tip surfaces 194 and 196 is a first planar side surface 198 and a second planar side surface 200 that is opposite to the first planar side surface 198. The insertion tools 170, 190, 210 are sized such that they can be received within a bone hole, as described herein. For example, the distance from the first side 176 to the second side 178 is less than a diameter of a bone hole sized for receipt of one of the disclosed flexible main body members 12, 42, 52, 72, 92, 102, 122, 132, 152. The distance from the first side 176 to the second side 178 can also be configured such that the insertion tools 170, 190, and 210 will contact a sloped interior bone hole surface, such as interior surface 316 described herein, at a predetermined depth to act as a stop, thereby allowing the flexible main body members 12, 42, 52, 72, 92, 102, 122, 132, 152 to be implanted at a predetermined depth. The insertion tools 170, 190, 210 are thus particularly useful for implanting the flexible main body members 12, 42, 52, 72, 92, 102, 122, 132, 152 during arthroscopic procedures, as well as during open procedures.

With additional reference to FIG. 12, another insertion tool according to the present teachings is generally illustrated at reference numeral 210. The insertion tool 210 includes a handle portion 212 that is similar to the handle 172 of the insertion tool 170, and thus like reference numbers are used to designate the similar features. Extending from the distal end 174 of the handle 172 at the first side 176 is a first retention surface 214. Extending from the distal end 174 at the second side 178 is a second retention surface 216. The first retention surface 214 and the second retention surface 216 are arranged opposite to one another and spaced apart to define a retention aperture 218 therebetween. At a distal end of the first retention surface 214 is a first tab 220 and at a distal end of the second retention surface 216 is a second tab 222. The first tab 220 and the second tab 222 extend toward one another and define an opening 224 of the retention aperture 218.

The various features of the insertion tools 170, 190, and 210 can be interchanged to provide configurations in addition to those illustrated in FIGS. 10-12. For example, the pointed conical tip 188 of the insertion tool 170 can be replaced with the pointed tip 192 of the insertion tool 190.

The first and second retention surfaces 184 and 186 of the insertion tool 170 can be provided at the distal end 174 of the insertion tool 190.

With additional reference to FIGS. 13A and 13B, implantation of the flexible fixation assembly 10 of FIG. 1 into a bone hole 300 will now be described. The bone hole 300 is formed or drilled into both a cortical bone layer 302 and a cancellous bone layer 304 of the bone hole 300. The bone hole 300 defines an opening 306 thereof at an exterior surface 308 of the cortical bone layer 302. A first portion 310 of the bone hole 300 proximate to the opening 306 is generally cylindrical and defines a uniform cylindrical surface. A second portion 312 of the bone hole 300 distal to the opening 306 tapers from the first portion 310 to a tip 314 that is at an end of the bone hole 300 opposite to the opening 306. The bone hole 300 thus conserves bone and is optimized to facilitate retention of the flexible main body members 12, 42, 52, 72, 92, 102, 122, 132, 152 described herein within the bone hole 300. However, the bone hole 300 can be defined to have any suitable shape and/or size. The bone hole 300 can be formed at any location where tissue is desired to be connected to the bone, for example.

To insert the flexible main body 12 into the bone hole 300, any of the insertion tools 170, 190, or 210, or any outer suitable insertion tool, can be used. As illustrated, the insertion tool 210 can be orientated such that the first tab 220 and the second tab 222 are on opposite sides of the suture anchor 26 approximately equidistant between the first end 30A and the second end 30B of the collapsible sleeve 28. The flexible main body 12 is positioned between the suture 14 and the opening 306 of the bone hole 300 with the flexible main body in the unflexed condition (first configuration). As the insertion tool 210 is pushed into the bone hole 300, the insertion tool 210 pushes the suture anchor 26 through the aperture of the suture engagement portion 24 and pushes the flexible main body 12 into the bone hole 300. As the flexible main body 12 is pushed into the bone hole 300, the flexible main body 12 moves from the unflexed position (first configuration) to the flexed position (second configuration) when the flexible main body 12 contacts the portion of the bone hole 300 at the opening 306 and contacts the interior surface 316 of the bone hole 300.

The suture anchor 26 expands at the second surface 18 of the flexible main body 12 and the first and second ends 30A and 30B contact the second surface 18 to restrict the suture anchor 26 from passing back through the aperture of the suture engagement portion 24. In the bone hole 300, the flexible main body 12 folds inward towards the axis A such that at least a majority of the second surface 18 contacts an interior surface 316 of the bone hole 300. Because the flexible main body 12 has a smaller cross-section at the inner edge 22 than at the outer peripheral edge 20, the portion proximate to the inner edge 22, which is inserted within the bone hole 300 first, will enter the bone hole 300 more freely than the portion proximate to the outer peripheral edge 20. As the portion proximate to the outer peripheral edge 20 is pushed deeper and deeper within the bone hole 300, the flexible main body 12 compresses more tightly against the interior surface 316 of the bone hole 300 to enhance retention of the flexible main body 12, as well as the suture 14, within the bone hole 300.

To more securely retain the flexible main body 12 within the bone hole 300, after the flexible main body 12 expands outward from the longitudinal axis A to abut the undersurface of the cortical bone layer 302, the flexible main body 12 is pulled slightly out from within the bone hole 300 such that the flexible main body 12 is further pressed against the undersurface of the cortical bone layer 302 to "lock" the flexible main body 12 within the bone hole 300. Any of the other flexible main body members 42, 52, 72, 92, 102, 122, 132, and 152 can be "locked" in a similar manner. The force to set the flexible main body members 42, 52, 72, 92, 102, 122, 132, and 152 can vary from about 4 lbs. to about 20 lbs., and their anchor strength can be about 8 lbs. to about 200 lbs. The flexible main body 12 is inserted within the bone hole 300 to a depth such that the outer peripheral edge 20 of the flexible main body 12 is beneath the cortical bone layer 302 and abuts an undersurface of the cortical bone layer 302, as illustrated in FIG. 13B, to enhance fixation of the flexible main body 12 within the bone hole 300. Thus, the flexible main body 12 secures the suture 14 within the bone hole 300 without the need for additional fastening devices or members, such as a screw, pin, adhesive, etc.

The flexible main body 12 secures the suture 14 such that the suture 14 can be slid within the aperture 24 by pulling on either end of the suture 14. Pulling on the suture 14 adjusts the suture 14 to facilitate cooperation of the suture 14 to, for example, tissue 318 in order to couple the tissue 318 (FIG. 14B) to the exterior bone surface 308. This slidable adjustment of the suture 14 further facilitates tying a knot 112 in the suture 14 to couple the suture 14 to the tissue 318. The ability to slidably adjust the suture 14 is particularly helpful during arthroscopic procedures. Each of the other flexible fixation assemblies 40, 50, 70, 90, 100, 120, 130, and 150 described herein also permit slidable adjustment of the sutures coupled thereto.

With additional reference to FIGS. 14A and 14B, implantation of the flexible fixation assembly 40 of FIG. 2 into the bone hole 300 will now be described. As illustrated, the insertion tool 190 is used to implant the flexible fixation assembly 40, but either the insertion tool 170 or the insertion tool 210 can also be used, as can be any other suitable insertion tool. The insertion tool 190 is orientated with the pointed tip 192 at the axial center of the flexible main body 42 and the flexible main body 42 is positioned just above the opening 306 of the bone hole 300. The suture 44 is threaded through the first aperture 46A and the second aperture 46B as illustrated. The flexible main body 42 is pushed into the bone hole 300 using the insertion tool 190. The pointed tip 192 engages the flexible main body 42 to facilitate cooperation between the insertion tool 190 and the flexible main body 42, which enhances the ability to manipulate the position of the flexible main body 42 within the bone hole 300 using the insertion tool 190. Once implanted within the bone hole 300, the flexible main body 42 expands outwards to contact the interior surface 316 of the bone hole 300 in a manner similar to that described above with respect to the flexible main body 42, and retain both the flexible main body 42 and the suture 44 within the bone hole 300.

With reference to FIGS. 15A and 15B, implantation of the flexible fixation assembly 50 of FIG. 3 will now be described. As illustrated, the insertion tool 190 is used to implant the flexible fixation assembly 50, but either the insertion tool 170 or the insertion tool 210 can also be used, as can be any other suitable insertion tool. The insertion tool 190 is orientated with the pointed tip 192 at the suture engagement portion 56 and the flexible main body 52 is positioned just above the opening 306 of the bone hole 300. The first and the second portions 58A and 58B of the suture 54 extend through the aperture 56 and the coupling member 60 is arranged on the side of the flexible main body 52 that enters the bone hole 300 first. The flexible main body 52 is pushed into the bone hole 300 using the insertion tool 190. The pointed tip 192 extends through the suture engagement portion 56 to facilitate cooperation between the insertion tool 190 and the flexible main body 52. When implanted in the bone hole 300, the coupling member 60 is arranged at the tip 314 and the flexible main body 52 is arranged between the coupling member 60 and the opening 306. The flexible main body 52 expands outward to press against the bone hole 300 and retain the flexible main body 52 in the bone hole in a manner similar to that described above with respect to the flexible main body 12.

With reference to FIGS. 16A and 16B, implantation of the flexible fixation assembly 70 will now be described. As illustrated, the insertion tool 210 is used to implant the flexible fixation assembly 70, but any other suitable insertion tool can be used, such as the insertion tools 170 or 190. The insertion tool 210 is coupled to the flexible main body 72 such that the first retention surface 214 abuts the first tapered side surface 80 and the second retention surface 216 abuts the second side surface 82 at the line D, which is the most narrow portion of the flexible main body 72. With the flexible main body 72 coupled thereto, the insertion tool 210 is then pushed into the bone hole 300, which causes the flexible main body 72 to fold along the line D such that one of the first or second generally planar surfaces 76 or 78 contact the interior surface 316 of the bone hole 300. Because the flexible main body 72 extends further outward from the longitudinal axis E at the first end 84 and the second end 86, greater compressive force will be exerted against the interior surface 316 of the bone hole 300 at the first and the second ends 84 and 86 than at the more narrow portion of the flexible main body 72 proximate to the line D, which enhances fixation of the flexible main body 72 within the bone hole 300. This description of the implantation of the flexible fixation assembly 70 is also sufficient to describe implantation of the flexible fixation assembly 90 illustrated in FIGS. 17A and 17B.

With additional reference to FIGS. 18A and 18B, implantation of the flexible fixation assembly 100 will now be described. The flexible main body 102 is arranged over the opening 306 of the bone hole 300 and, as illustrated, the insertion tool 190 is used to implant the assembly 100 into the bone hole 300; however, any other insertion tool including the tools 170 and 210 can be used as well. The pointed tip 192 is inserted against or through the first and second sutures 104 and 106 at the center of the flexible main body 102 where the first and the second sutures 104 and 106 overlap. Use of more than one suture allows for more repair options, more points of fixation in tissue, bone conservation, and can reduce costs. As illustrated in FIG. 18B, the flexible main body 102 folds and compresses in a manner that is substantially similar to that described above with respect to the flexible main body 12 to secure the flexible main body 102 within the bone hole 300 and anchor both the first suture 104 and the second suture 106 therein. This description of the implantation of the flexible fixation assembly 100 is also sufficient to describe implantation of the flexible fixation assembly 120 illustrated in FIGS. 19A and 19B.

With additional reference to FIGS. 20A and 20B, implantation of the flexible fixation assembly 130 will now be described. The flexible main body 132 is st wrapped over the suture such that the first portion 136 overlaps the second portion 140. As illustrated, the insertion tool 170 is used to implant the flexible fixation assembly 130 within the bone hole, but any other suitable insertion tool can be used, including the insertion tools 190 and 210. Prior to implantation, the flexible main body 132 is can be orientated such that the first end portion 138 is facing the opening 306 of the bone hole 300 to help prevent the flexible main body 132 from becoming unwrapped. The pointed conical tip 188 of the insertion tool 170 is inserted through the flexible main body 132 and the suture 134 to mount the flexible main body 132 thereto for insertion. As the flexible main body 132 is inserted within the bone hole 300, the first side 146 and the second side 148 fold together and the flexible main body 132 is biased outward against the interior surface 316 of the bone hole 300 to retain the first end 332 and the suture 134 extending therethrough within the bone hole 300.

With additional reference to FIGS. 21A and 21B, implantation of the flexible fixation assembly 150 will now be described. The flexible main body 152 is arranged such that the suture 154 abuts or is in close proximity to the concave inner surface 158. The suture 154 can be fixedly secured to the flexible main body 152 prior to implantation, or can be couple thereto with the insertion tool 170, as illustrated in FIG. 21A, by inserting the pointed conical tip 188 first through the flexible main body 152 into the suture 154. Any other suitable insertion tool can be used as well, including the insertion tool 190 or the insertion tool 210. To implant the flexible fixation assembly 150 within the bone hole 300, the assembly 150 is arranged such that the concave inner surface 158 faces the opening 306 and the suture 154 extends across the opening 306 between the concave inner surface 158 and the opening 306. The flexible fixation assembly 10 is pushed into the bone hole 300 using the insertion tool 170 such that the suture 154 first is implanted within the bone hole 300 and the concave inner surface 158 pushes the suture 154 against the interior surface 316 of the bone hole 300. The flexible main body 152 is biased against the interior surface 316 to secure the flexible fixation assembly 150 within the bone hole 300.

Any suitable implant/graft can be anchored in the bone hole 300, at the exterior surface 308 of the bone, or proximate to the exterior surface 308 with any of the sutures described herein, such as the sutures 14, 74, 94, 106, 134, or 154, once the flexible main body 12, 72, 92, 102, 122, 132, 152 associated therewith is implanted within the bone hole 300. For example, the graft may be a graft used in ACL repair, soft tissue attachment to bone, rotator cuff repair, labrum repair, etc.

Figures 22, 23:
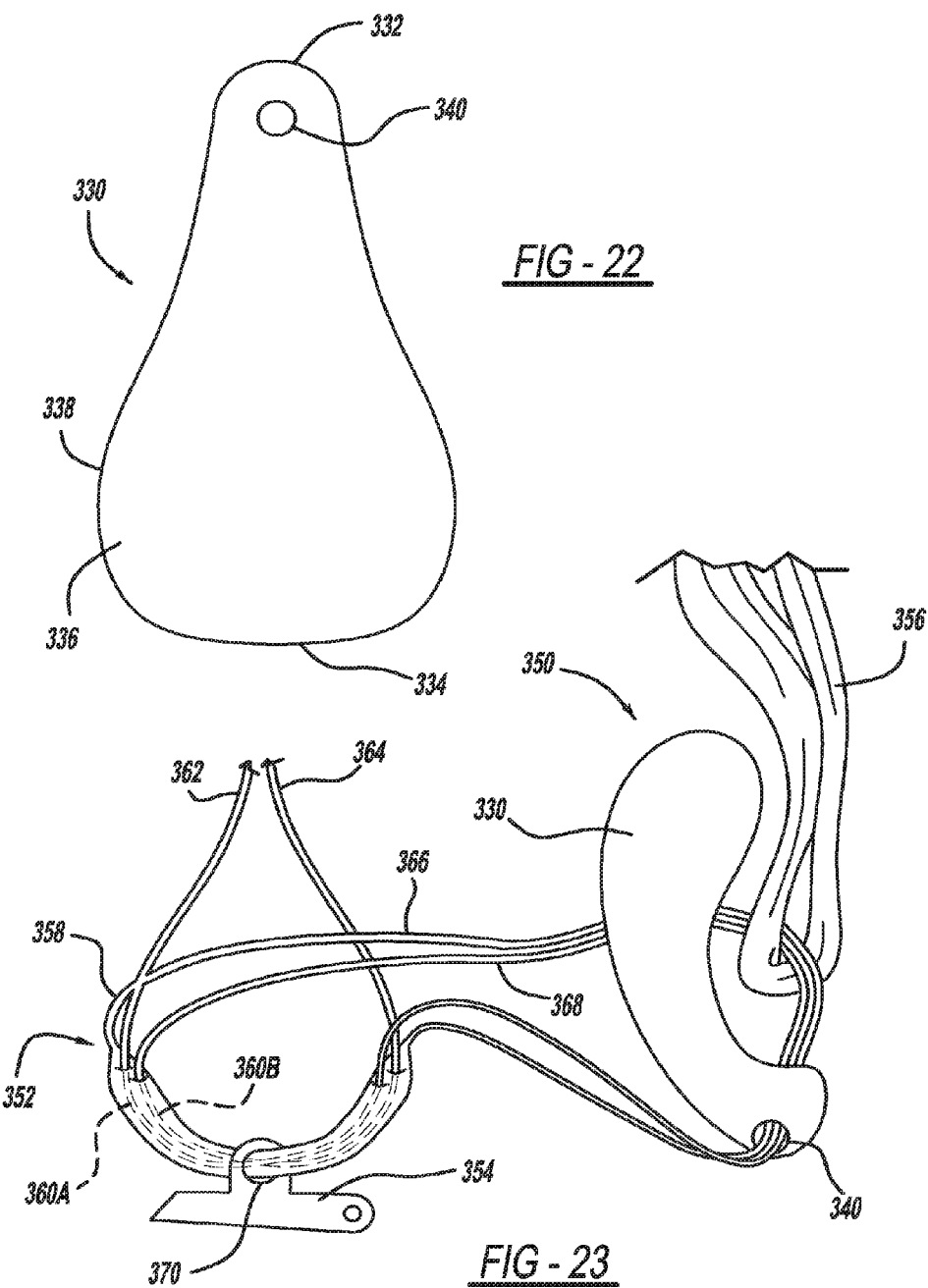
FIG. 22 is a planar view of a flexible main body of another flexible fixation assembly according to the present teachings.
FIG. 23 illustrates a flexible fixation assembly according to the present teachings including the flexible main body of FIG. 22.

With additional reference to FIG. 22, a flexible main body 330 for use with the flexible fixation assembly 350 of FIG. 23 is illustrated. The flexible main body 330 is generally shaped as a pear or teardrop, and includes a first end 332 and a second end 334. The first end 332 is generally more narrow than the second end 334. The flexible main body 330 tapers outward from the first end 332 to the second end 334. Between the first end 332 and the second end 334 is a first side 336 and a second side 338 that is opposite to the first side 336. The flexible main body 330 defines a suture engagement portion 340 at the first end 332 that extends between the first side 336 and the second side 338. The flexible main body 330 can be made of the same material described above with respect to the flexible main body 12.

With additional reference to FIG. 23, the flexible fixation assembly 350 further includes an adjustable suture construct 352, an anchor 354, and a graft 356. The adjustable suture construct 352 can be any suitable adjustable suture construct, such as the Zip-Loop™ suture construct by Biomet, Inc. of Warsaw, Ind. U.S. Pat. No. 7,658,751 issued Feb. 9, 2012 and U.S. Pat. No. 7,601,165 issued Oct. 13, 2009 also disclose a number of suture constructs that can be used, and are incorporated by reference herein. The suture construct 352 includes a suture 358 that defines a pair of longitudinal passages 360A and 360B. A first end 362 and a second end 364 of the suture 358 are passed through different ones of the longitudinal passages 360A and 360B to define a first loop 366 and a second loop 368 of the suture 358. The suture construct 352 is arranged such that the portion defining the longitudinal passages 360A and 360B extend through an aperture 370 defined by the anchor 354. The graft 356 is inserted through, and folder over, the first loop 366 and the second loop 368. The flexible main body 330 is arranged between the anchor 354 and the graft 356 with the portions of the suture 358 defining the first loop 366 and the second loop 368 extending through the suture engagement portion 340.

Figure 24A:
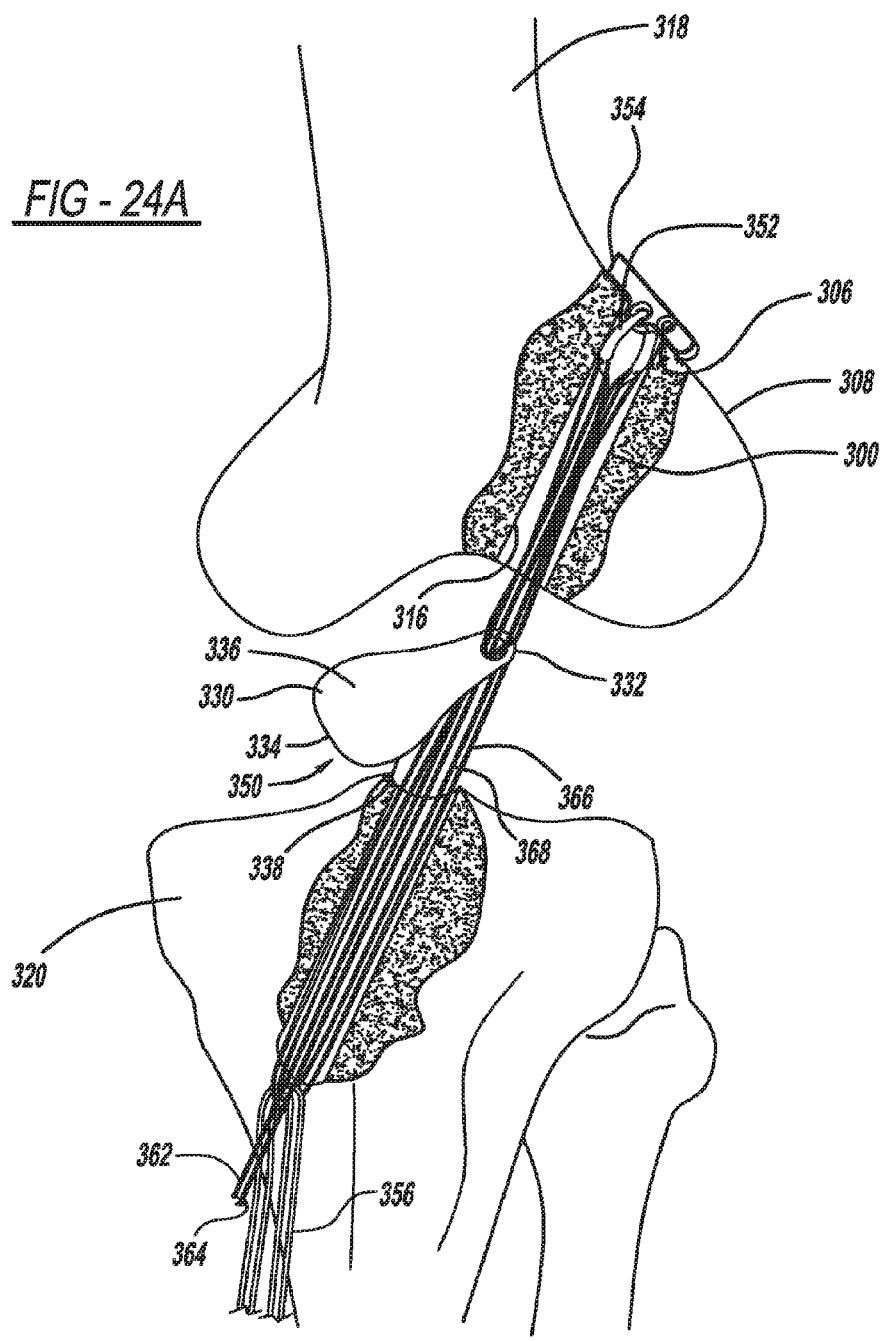
FIGS. 24A and 24B illustrate insertion of the flexible fixation assembly of FIG. 23 within a bone hole.
Figure 24B:
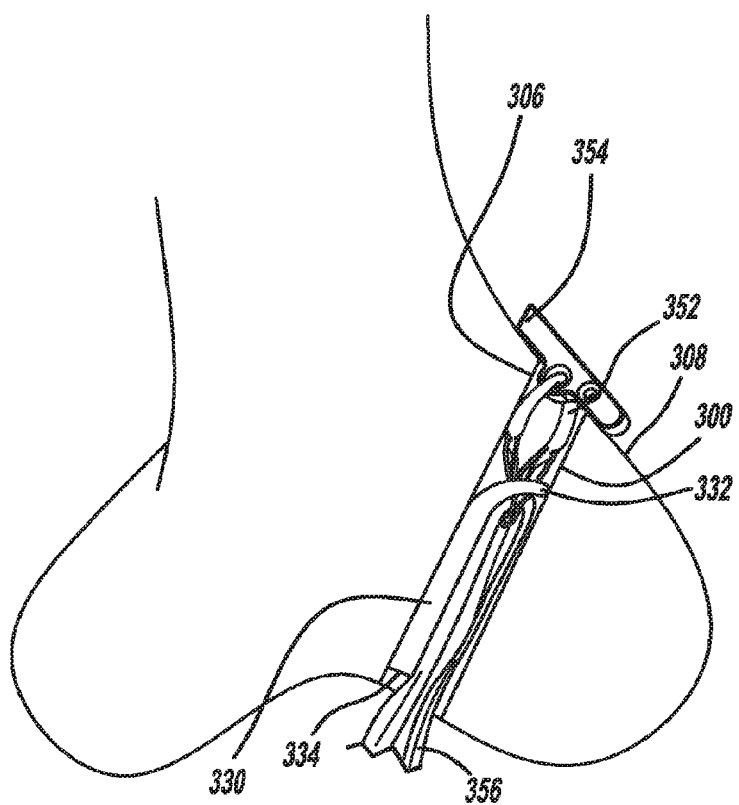

With additional reference to FIGS. 24A and 24B, implantation of the flexible fixation assembly 350 will now be described. The flexible fixation assembly 350 can be used with a variety of surgical procedures, such as ACL replacement in a femur 318 and a tibia 320. The anchor 354 is first seated on the exterior bone surface 308 at the opening 306 of the bone hole 300. The adjustable suture construct 352 is orientated to extend through the bone hole 300. Any suitable anchor can be used, such as any one of the anchors disclosed in U.S. Pat. No. 7,500,983 issued Mar. 10, 2009, which is incorporated herein by reference. Outside of the bone hole 300 beyond an end opposite to the exterior bone surface 308 is the flexible main body 330 and the graft 356, as illustrated in FIG. 24A. The first end 362 and the second end 364 of the suture 358 are pulled to decrease the size of the first and the second loops 366 and 368, thereby pulling the flexible main body 330 and the graft 356 into the bone hole 300. The adjustable suture construct 352 retains the graft 356 and the flexible main body 330 within the bone hole 300 without the need for tying knots, as described in U.S. patent application Ser. No. 13/109,672 filed on May 17, 2011 for example, which is incorporated herein by reference. At the second end 334 of the flexible main body 330, the flexible main body 330 is wider than first end 332. The flexible main body 330 can assist with fixing the graft 356 in the hole 300 by pressing distal aspects of the graft 356 against the hole 300, can act as a plug to prevent infiltration of synovial fluid, can increase strength of stiffness, can aid in incorporation of the graft 356 in bone, can carry Biologic elements, and can act as a bone void filler.

The end of the graft 356 opposite to the adjustable suture construct 352 is attached to the tibia bone 320 as is known in the art. Therefore, at the second end 334, the flexible main body 330 will bend and follow the curvature of the interior surface 316 of the bone hole 300. One of the first side 336 or the second side 338 of the flexible main body 330, whichever is arranged to face the interior surface 316, contacts the interior surface 316 of the bone hole 300 and presses the graft 356 against the wall of the bone hole 300. The flexible main body 330 can be used in any suitable procedure, such as ACL repair as illustrated.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for affixing a suture in a bone hole comprising:
    forming a bone hole in bone;
    positioning at the bone hole a flexible main body having a suture attached to a suture engagement portion of the flexible main body, the flexible main body including a first generally planar surface, a second generally planar surface opposite to and spaced apart from the first generally planar surface, and a side surface extending between the first generally planar surface and the second generally planar surface; and
    implanting within the bone hole the flexible main body with the suture coupled thereto using an insertion tool such that the first generally planar surface and the second generally planar surface each move to a collapsed non-planar position as implanted, the flexible main body configured to flex outward against walls of the bone hole to retain the flexible main body and the suture coupled thereto within the bone hole, wherein an entirety of the side surface moves radially towards a longitudinal axis extending through an axial center of the flexible main body when the flexible main body is inserted in the bone hole.

2. The method of claim 1, further comprising positioning at the bone hole the flexible main body with the suture coupled to the suture engagement portion with a suture anchor.

3. The method of claim 1, further comprising positioning at the bone hole the flexible main body with the suture coupled to the suture engagement portion by threading the suture through a first aperture and a second aperture of the flexible main body.

4. The method of claim 1, further comprising positioning at the bone hole the flexible main body with the suture coupled to the suture engagement portion with a coupling member of the suture, the coupling member including a larger diameter than a diameter of an aperture of the suture engagement portion through which the suture extends, the aperture defined by the flexible main body.

5. The method of claim 1, further comprising positioning at the bone hole the flexible main body with the suture coupled to the suture engagement portion by weaving the suture through slits defined in the main body.

6. The method of claim 1, further comprising:
    implanting an anchor at an opening of the bone hole, the suture is a suture construct coupled to the anchor;
    coupling a graft to a loop of the suture construct; and
    pulling on two ends of the suture construct to draw the graft into the bone hole.

7. A method for affixing a suture in a bone hole comprising:
    forming a bone hole in bone;
    positioning at the bone hole a flexible main body having a suture coupled thereto, the flexible main body in a first configuration in which a first surface and a second surface opposite to the first surface are each generally planar with a side surface extending between the first surface and the second surface;
    inserting the flexible main body with the suture coupled thereto in the bone hole with an insertion tool such that as the flexible main body is inserted the flexible main body folds at a point where the insertion tool is connected to the flexible main body to provide the flexible main body with a second configuration in which the first surface and the second surface are not planar and wherein an entirety of the side surface moves radially towards a longitudinal axis extending through an axial center of the flexible main body when the flexible main body is inserted in the bone hole; and coupling soft tissue to the suture to secure the soft tissue within or proximate to the bone hole.

8. The method of claim 7, further comprising connecting the insertion tool to the flexible main body by inserting a pointed tip of the insertion tool through the flexible main body and the suture.

9. The method of claim 7, further comprising connecting the insertion tool to the flexible main body by inserting the flexible main body within an aperture of the insertion tool.

10. The method of claim 7, further comprising inserting the flexible main body in the bone hole such that an edge of the flexible main body abuts an inner surface of a cortical layer of the bone.

11. The method of claim 7, further comprising pulling on the suture after the flexible main body has been inserted in the bone hole to pull the flexible main body against an inner surface of a cortical bone layer to further secure the flexible main body in the bone hole.

12. The method of claim 7, wherein the soft tissue is one of an ACL, labrum, or rotator cuff.

* * * * *